United States Patent [19]

Takahashi

[11] 4,361,042
[45] Nov. 30, 1982

[54] DIGITAL TYPE ULTRASONIC HOLOGRAPHY APPARATUS

[75] Inventor: Fuminobu Takahashi, Hitachi, Japan
[73] Assignee: Hitachi, Ltd., Tokyo, Japan
[21] Appl. No.: 225,993
[22] Filed: Jan. 19, 1981
[30] Foreign Application Priority Data
  Jan. 21, 1980 [JP] Japan ................................. 55-4640
[51] Int. Cl.³ ............................................. G01N 29/04
[52] U.S. Cl. ............................................. 73/603; 73/613
[58] Field of Search ................ 73/603, 604, 610, 611, 73/613; 367/7, 8

[56] References Cited
U.S. PATENT DOCUMENTS
  4,222,273  9/1980  Takahashi et al. ................... 73/603
FOREIGN PATENT DOCUMENTS
  18079  10/1980  European Pat. Off. ............. 73/603

Primary Examiner—Stephen A. Kreitman
Attorney, Agent, or Firm—Antonelli, Terry & Wands

[57] ABSTRACT

A digital type ultrasonic holography apparatus includes a clock generator for generating a clock pulse signal having a fixed period, a transducer for transmitting spike-like ultrasonic pulses toward an object in synchronism with trigger pulses derived through the frequency division of the clock pulse signal and receiving the reflected wave from the object, a waveform shaping circuit for shaping the received wave into a digital pulse signal, a coincidence detecting circuit for narrowing the pulse width of the digital pulse signal to a magnitude shorter than the period of the clock pulse signal and judging whether or not the pulse width-narrowed digital pulse is present at the level-changing time of the clock pulse signal, thereby to generate a coincidence signal, a scanner for scanning the transducer, and a device for displaying a hologram of the object in accordance with the value of the coincidence signal and the scanning of the transducer. The ratio of the interference fringe occupied portion of the displayed hologram to the remaining portion thereof is determined by the narrowed pulse width of the digital pulse.

7 Claims, 6 Drawing Figures

DIGITAL TYPE ULTRASONIC HOLOGRAPHY APPARATUS

The present invention relates to an apparatus in which the forms and positions of cracks involved in an object such as a metallic member are recognized by means of an ultrasonic hologram.

The conventional ultrasonic holography apparatus obtains the information on cracks in an object by transmitting ultrasonic pulses (transmission wave) of sine mode from a transducer to the object, receiving a reflected wave from the object (hereinafter referred to simply as "object-modified wave"), causing the object-modified wave to interfere with a reference wave having a predetermined phase difference from the transmission wave to obtain an interference wave, and luminance-modifying the amplitude of the interference wave to produce an ultrasonic hologram of the object.

On the other hand, U.S. Pat. No. 4,222,273 discloses a digital type ultrasonic holography apparatus in which an ultrasonic wave is transmitted to an object in connection with a clock pulse signal having a 0-1 level pattern and a duty ratio of 50%, the object-modified wave from the object is converted into a digital pulse signal, and a coincidence signal is generated on the basis of the level of the clock pulse signal at the rising or falling time instant of the digital pulse signal to produce a hologram having a binary pattern which assumes a state of "1" or "0" according to whether or not the coincidence signal is generated. This apparatus is superior to the above-mentioned conventional apparatus in that the time resolution capacity for discriminating a plurality of object-modified waves is high and in that a distance between adjacent interference fringes on the hologram can be readily controlled without changing the frequency of the ultrasonic transmission wave used.

An object of the present invention is to provide a digital type ultrasonic holography apparatus which can maintain the advantages of the digital type holography apparatus while diminishing a possible inconvenience that a produced hologram is liable to be disturbed by noises.

If in the above-mentioned known digital type holography apparatus a noise signal additionally enters a transmission line for transmitting the digital pulse indicative of the reception of an object-modified wave, the probability that a spurious signal may be outputted at the leading or trailing edge of the noise signal is equal to the duty ratio of the clock pulse signal (usually set to 0.5). Accordingly, there is a very large possibility of the hologram being disturbed by the noise signal.

In the digital type ultrasonic holography apparatus according to the present invention, the received object-modified wave is shaped into a digital pulse signal having a predetermined pulse width shorter than the period of the clock pulse signal, and a coincidence signal used for producing a hologram is generated when the digital pulse is present within a preselected time interval and at a predetermined level-changing time of the clock pulse signal such as the leading or trailing edge thereof.

With such a construction, the probability p that a coincidence signal is generated due to a noise signal entering a digital pulse signal transmission line is given by $$p = \tau_n / T$$

wherein $\tau_n$ is the pulse width of the noise signal, and T the period of the clock pulse signal. Therefore, if the clock pulse signal having a frequency of several MHz is used, a sufficiently precise hologram can be produced. The pulse width of the electric noise signal is usually less than several nanoseconds. Assuming that the frequency of the clock pulse signal is 3 MHz and the pulse width $\tau_n$ of the noise signal is 10 nanoseconds, the probability p is equal to 0.03. That is, a possibility of the coincidence signal being generated due to the electric noise signal is very small. Thus, the apparatus according to the present invention can produce a low-noise, clear and accurate hologram.

The present invention will now be described in conjunction with the accompanying drawings, in which:

FIG. 1 shows the whole circuit construction of an embodiment of the present invention. The present embodiment exemplifies the case where the present invention is applied to a pulse echo system, in which the transmission and reception of ultrasonic wave are made by means of a single transducer.

Figure 1:
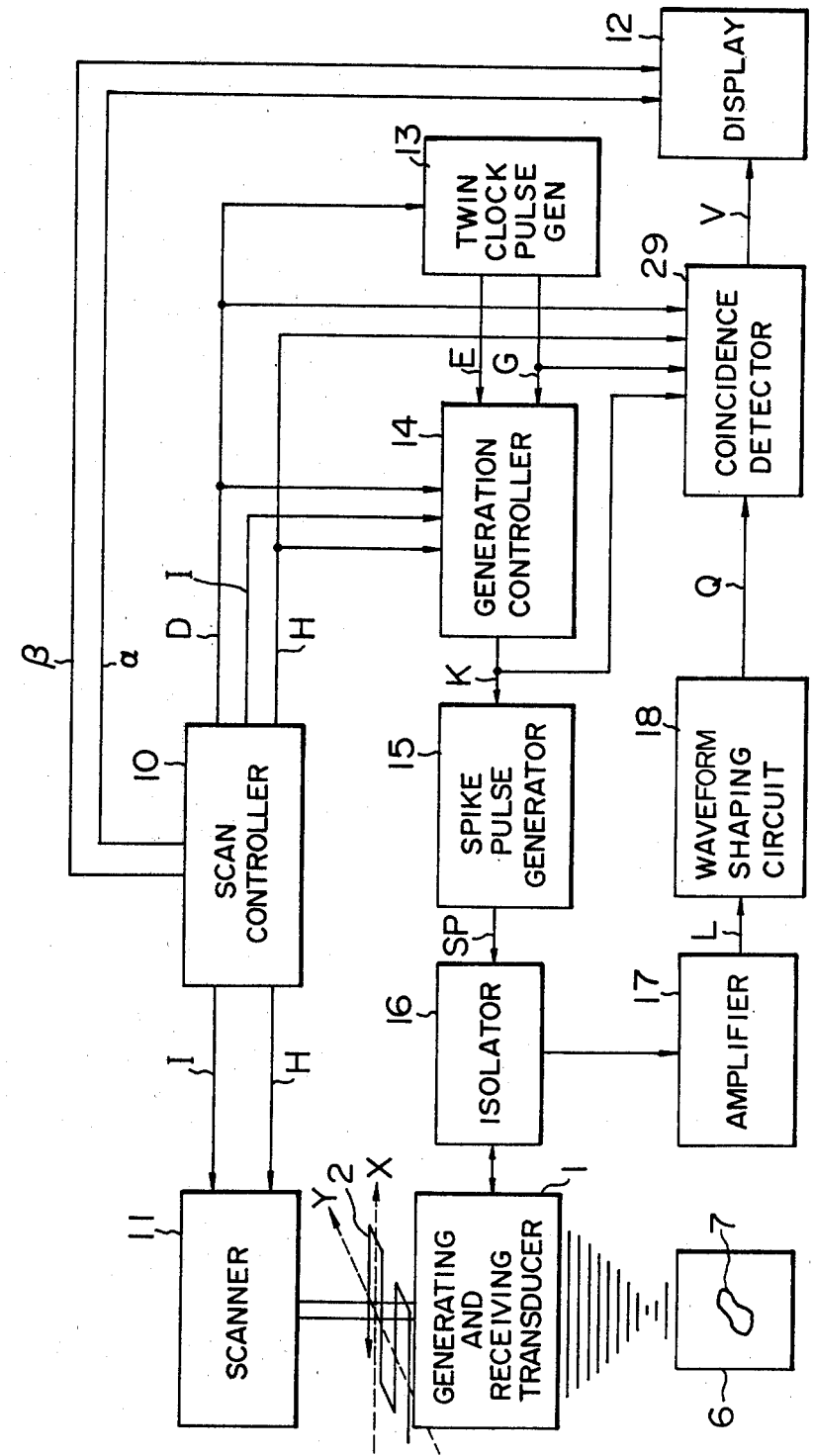
FIG. 1 is a block diagram showing an embodiment of a digital type ultrasonic holography apparatus according to the present invention.
Figure 2:
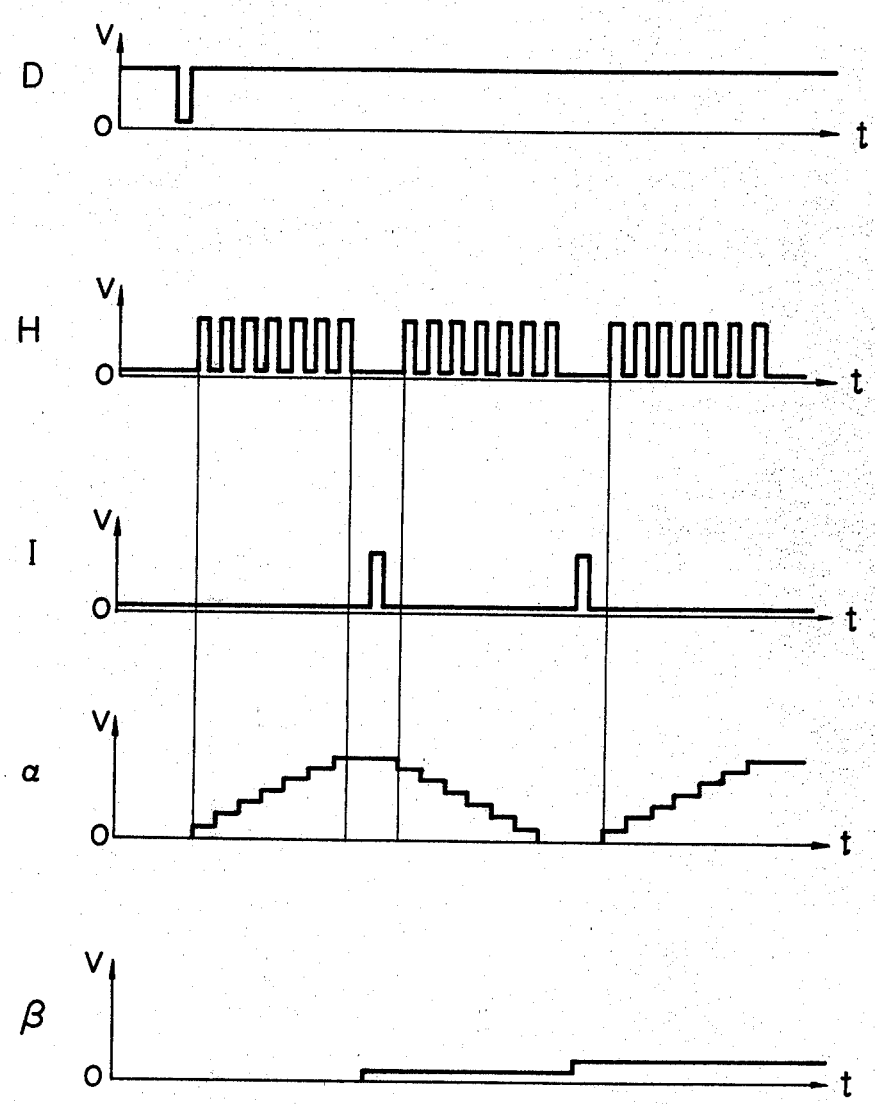
FIGS. 2 and 3 are time charts for showing the waveforms of signals appearing at various parts in the apparatus shown in FIG. 1.

Referring to FIG. 1, a scanner 11 causes a transducer 1 to scan an X-Y plane along a scanning path 2. A scan controller 10 supplies X and Y drive pulses H and I as control signals to the scanner 11 to drive the scanner 11. The scan controller 10 also produces X-coordinate and Y-coordinate signals $\alpha$ and $\beta$ indicative of the position of the transducer 1. Further, the scan controller 11 delivers a reset pulse D when the scanning operation is started. The X-coordinate signal $\alpha$ and the Y-coordinate signal $\beta$ are respectively obtained by accumulating the X drive pulses H and the Y drive pulses I supplied after the reset pulse D and subjecting the accumulated pulses to D-A conversion. The waveforms of the signals H, I, D, $\alpha$ and $\beta$ are shown in FIG. 2.

A twin clock pulse generator 13 generates a clock pulse signal G having a frequency of 3 MHz, which corresponds to the reference wave in the conventional holography apparatus, and a clock pulse signal E having a frequency of 12 MHz which is a fundamental clock pulse signal used for forming the clock signal G and is further used for delaying the generation or transmission phase of ultrasonic pulse in accordance with the scanning operation by the transducer 1.

A generation controller 14 produces a trigger pulse K every time a preselected number of clock pulses G are received from the generator 13. In usual, the trigger pulse K is generated in synchronism with the leading edge of the clock pulse G. In this case, there is produced a hologram equivalent to that obtained in the conventional holography apparatus when the angle of incidence of a reference wave is 0°. In particular cases, the trigger pulse K may be slightly delayed relative to the leading edge of the clock pulse G by a time corresponding to the number of X or Y drive pulses accumulated. In such cases, a produced hologram is equivalent to that obtained in the conventional apparatus when an obliquely incident reference wave is employed.

Figure 3:
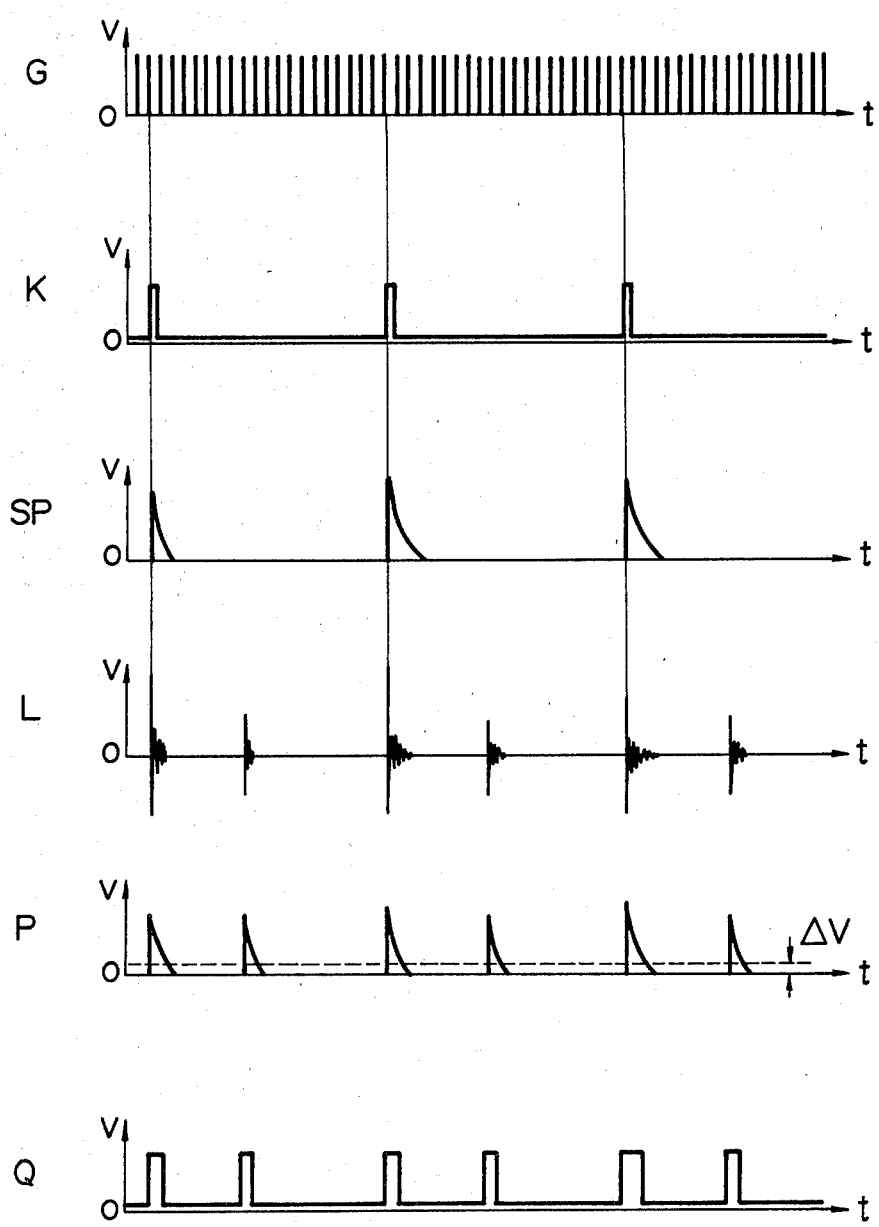

A spike pulse generator 15 generates a spike pulse SP in synchronism with the trigger pulse K. An isolator 16 supplies the spike pulse SP to the transducer 1. Then, the transducer 1 transmits an ultrasonic wave pulse to an object 6 in synchronism with the spike pulse SP, receives a reflected wave from the surface of and a crack 7 in the object 6, and produces an electric signal corresponding to the reflected wave. The electric signal is supplied through the isolator 16 to an amplifier 17. An amplified signal L from the amplifier 17 is supplied to a waveform shaping circuit 18. In the circuit 18, the amplified reflected-wave signal is detected and the detected signal P is then compared with a predetermined reference voltage $\Delta V$ to produce a received-wave pulse signal Q which is digitized with TTL level. The waveforms of the signals G, K, SP, L, P and Q are shown in FIG. 3.

The received-wave pulse signal Q thus obtained is applied to a coincidence detector 29. In the detector 29, the received-wave pulse signal Q is shaped into a pulse signal having a pulse width shorter than the period of the clock pulse signal G, to detect the coincidence in time between the thus shaped pulse and the leading edge of the clock pulse. A display device 12 receives the X- and Y-coordinate signals $\alpha$ and $\beta$ from the scan controller 10 as deflection signals for determining a position on a display screen and receives a coincidence signal V from the coincidence detector 29 as a luminance signal, so that a hologram is displayed on the display screen.

All of the above-mentioned circuits excepting the coincidence detector 29 are disclosed in the U.S. Pat. No. 4,222,273. Therefore, further explanation will be omitted.

Figure 4:
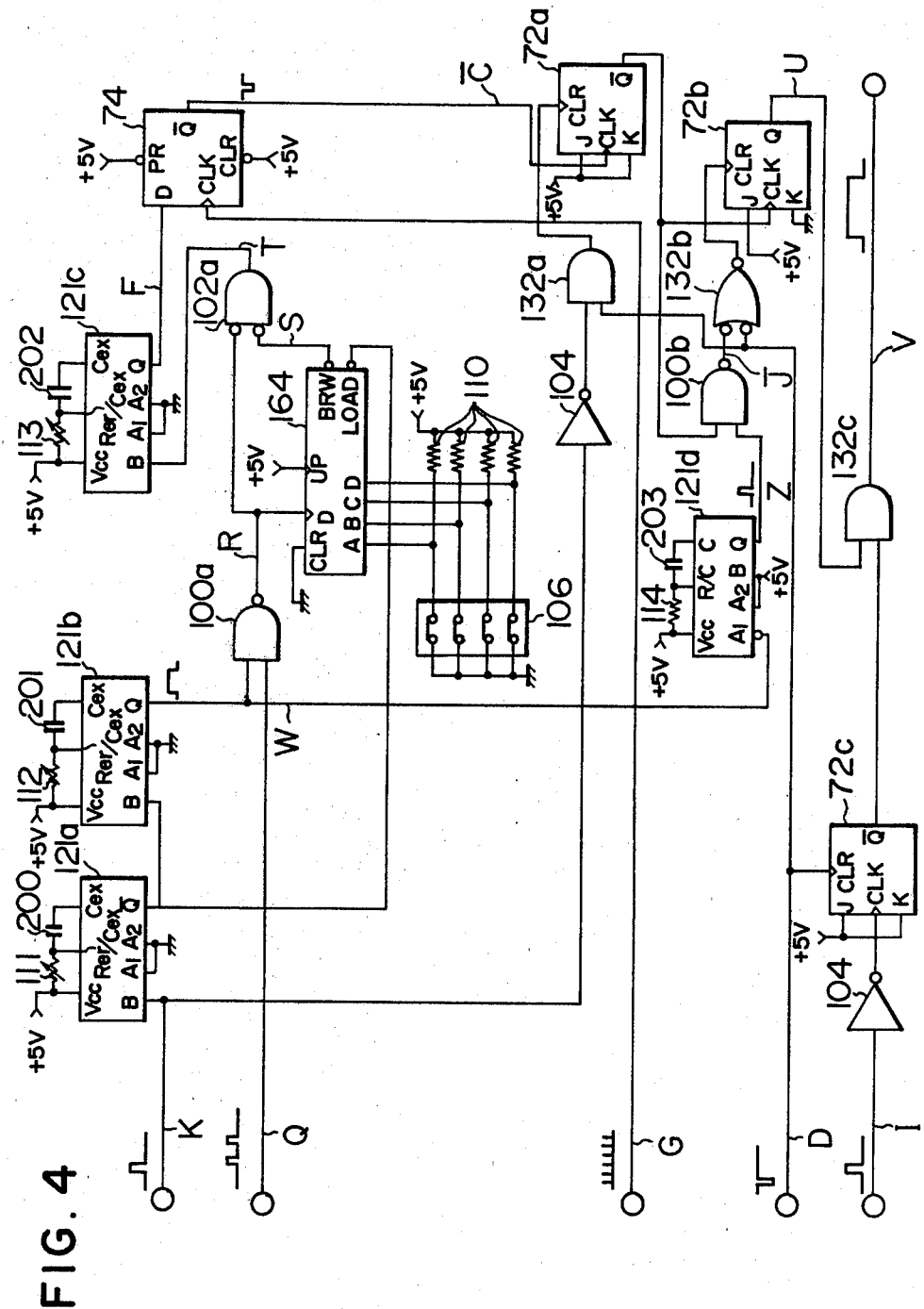
FIG. 4 is a circuit diagram showing a concrete example of the coincidence detector shown in FIG. 1.
Figure 5:
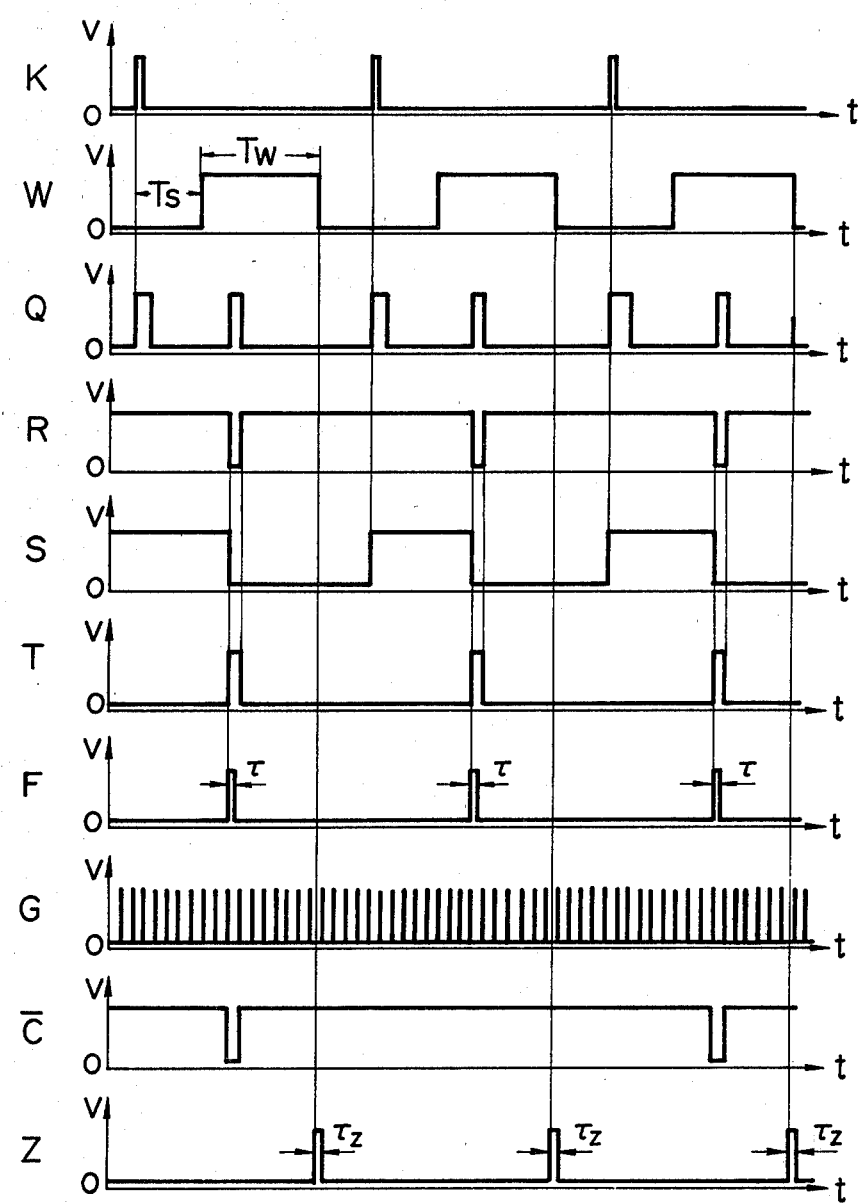
FIGS. 5 and 6 are time charts for showing the waveforms of signals at various parts shown in FIG. 4.
Figure 6:
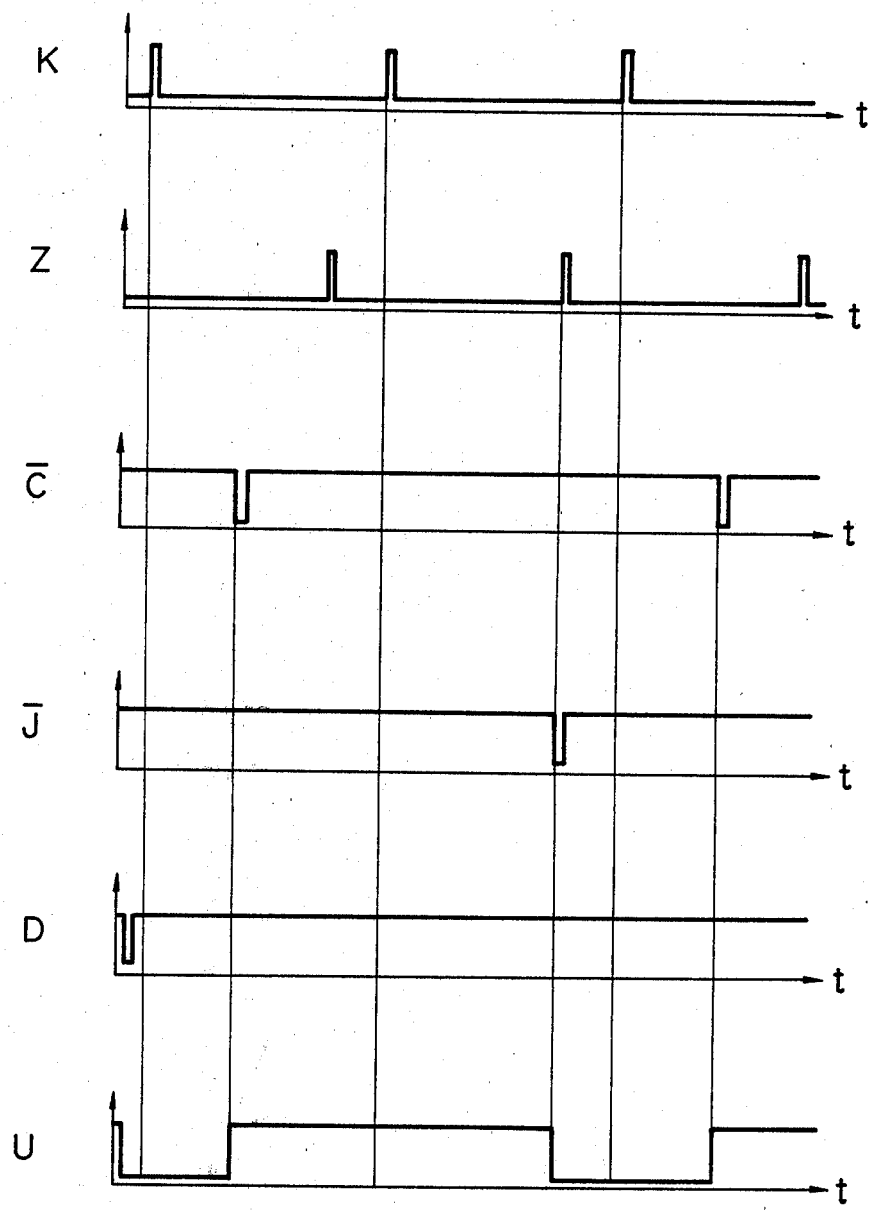

FIG. 4 exemplifies a detailed circuit configuration of the coincidence detector 29. FIGS. 5 and 6 show examples of waveforms of signals appearing at various parts shown in FIG. 4.

Referring to FIG. 4, the trigger pulse K, outputted from the generation controller 14 is applied to a circuit including cascade-connected monostable multivibrators 121a and 121b which in turn forms a time-gate pulse W appearing after the lapse of a predetermined time Ts from the leading edge of the trigger pulse (or the signal K) and taking the level of "1" for a predetermined time Tw. The time Ts is determined by the time constant of a circuit made up of a variable resistor 111 and a capacitor 200, while the time Tw is determined by the time constant of a circuit made up of a variable resistor 112 and a capacitor 201. The delay time Ts and pulse width Tw of the time-gate pulse W are selected so that the reflected wave from the object 6 can be received within the duration time of the time-gate pulse.

The received-wave pulse signal Q from the waveform shaping circuit 18 is applied to a NAND gate 100a together with the time-gate pulse signal W. Only, the received-wave pulses Q within a period when the time-gate pulse signal W is kept in the level of "1" can pass through the NAND gate 100a. The output R of the NAND gate 100a is applied to the down input of a 4-bit up-down counter 164. A barrow signal S from the counter 164 and the output R of the NAND gate 100a are supplied to a NOR gate 102a. Thus, only a specified n-th one of the received-wave pulses R which have passed through the NAND gate 100a is extracted in and passes through the NOR gate 102a. Reference numeral 106 designates a switching element for specifying or designating the number n. In the example illustrated in FIG. 5, only the first received-wave pulse is extracted, that is, n=1 (see signal T).

The thus extracted received-wave pulse T is applied to a monostable multivibrator 121c to be shaped into an object-modified wave pulse F whose leading edge is synchronized with that of the extracted pulse T and whose pulse width $\tau$ is made narrower than that of the extracted pulse T. The pulse width $\tau$ determined by the resistance of a variable resistor 113 and the capacitance of a capacitor 202 is selected to be shorter than the period of the clock pulse signal G.

The object-modified wave pulse signal F is applied to the data terminal of an edge trigger flip flop 74 which has the clock terminal applied with the clock pulse signal G. The edge trigger flip flop 74 holds the level of the object-modified wave pulse F at the leading edge of each clock pulse G. Accordingly, the flip flop 74 produces a negative logic coincidence pulse $\overline{C}$ only when the leading edge of the clock pulse G coincides with the object-modified wave pulse F.

The waveforms of the signals explained in conjunction with FIG. 4 are shown in FIG. 5. FIG. 5 shows the case where the negative logic coincidence pulses $\overline{C}$ are delivered in the respective periods corresponding to the first and third trigger pulses K and no coincidence pulse $\overline{C}$ is delivered in a period corresponding to the second trigger pulse K.

Again referring to FIG. 4, a monostable multivibrator 121d produces a gate-end pulse Z with a pulse width $\tau_z$ in synchronism with the trailing edge of the time-gate pulse W. The pulse width $\tau_z$ is determined by the resistance of a resistor 114 and the capacitance of a capacitor 203. On the other hand, a circuit including a NOT gate 104a, a NAND gate 100b, AND gates 132a, 132b and J-K flip flops 72a, 72b produces a signal U for display of the hologram of the object, on the basis of the trigger pulse signal K, the negative logic coincidence pulse signal C, the gate-end pulse signal Z and the reset pulse signal D. More specifically, the J-K flip flop 72a is reset when the reset pulse D or the trigger pulse K is received, and is set when the negative logic coincidence pulse $\overline{C}$ is received. Accordingly, the NAND gate 100b, applied with the $\overline{Q}$ output of the J-K flip flop 72a and the gate-end pulse (or the signal Z) delivers an anticoincidence pulse J when no negative logic coincidence pulse C is generated within the duration time of the time-gate pulse W. The clear terminal of the J-K flip flop 72b is applied with the reset pulse D and the anticoincidence pulse $\overline{J}$, and the clock-terminal thereof is applied with the $\overline{Q}$ output of the J-K flip flop 72a. Accordingly, the output signal U of the J-K flip flop 72b takes the level of "1" when the coincidence pulse $\overline{C}$ is generated and returns to "0" upon reception of the gate-end pulse Z when no coincidence pulse is generated. Further, the signal U is brought to the level of "0" when the reset pulse D is generated. The signals K, Z, $\overline{C}$, $\overline{J}$, D and U are shown in FIG. 6.

The thus obtained signal U is prevented from passing through an AND gate 132c during the period when the transducer 1 moves on the X-axis in a reverse or negative direction. In other words, the AND gate 132c is controlled by the $\overline{Q}$-output of a flip flop 72c which counts the Y drive pulses I supplied after the reset pulse D has been generated. A coincidence signal V passed through the gate 132c is applied to the display device 12 to be used as a luminance signal. According to this circuit arrangement, a hologram is displayed on the display device 12 only in a period when the transducer 1 moves on the X-axis in a positive direction. As a result, it is possible to prevent a shear in picture image which may be caused in a mechanical idle time of the scanner 11.

In the above-mentioned embodiment, the pulse width τ of the object-modified wave pulse signal F can vary with the resistance of the variable resistor 113 shown in FIG. 4. Therefore, the ratio of the interference fringe occupied portion of the hologram to the remaining portion thereof is controllable.

The resistance of the variable resistor 113 may be fixed so that the pulse width τ is equal to one-half the period T of the clock pulse signal G. In this case, the ratio of the interference fringe occupied portion of the hologram to the remaining portion thereof equals 1:1.

Further, it is easy to construct an apparatus in which a distance between adjacent interference fringes on the hologram is varied by changing the period T of the clock pulse G. In such an apparatus, it is desired to change the pulse width τ in accordance with the change of the period T of the clock pulse signal G.

What is claimed is:

1. A digital type ultrasonic holography apparatus comprising:
   first means for generating a clock pulse signal having a fixed period;
   second means for transmitting ultrasonic pulses toward an object in synchronism with trigger pulses derived through the frequency division of said clock pulse signal and for receiving an object-modified wave of said ultrasonic pulses from said object to convert said object-modified wave into an electric signal;
   third means for shaping said converted object-modified wave to produce an object-modified wave pulse signal having a predetermined pulse width shorter than said fixed period of said clock pulse signal; and
   fourth means for discriminating whether or not a pulse is present in said object-modified wave pulse signal at a predetermined level-changing time of said clock pulse signal and within a predetermined time portion of the repetition interval of said trigger pulses and for generating a coincidence signal when the presence is discriminated, said coincidence signal being used to produce a hologram of said object.

2. A digital type ultrasonic holography apparatus according to claim 1, wherein said predetermined level-changing time of said clock pulse signal is one selected from the leading and trailing edges thereof.

3. A digital type ultrasonic holography apparatus according to claim 1, wherein said predetermined pulse width of said object-modified wave pulse signal is approximately one-half said period of said clock pulse signal.

4. A digital type ultrasonic holography apparatus according to claim 1, further comprising fifth means for adjusting said pulse width of said object-modified wave pulse signal produced by said third means.

5. A digital type ultrasonic holography apparatus comprising:
   means for generating a clock pulse signal having a fixed period;
   a transducer for transmitting spike-like ultrasonic pulses toward an object in synchronism with trigger pulses derived through the frequency division of said clock pulse signal and for converting an object-modified wave of said ultrasonic pulses from said object into an electrical signal;
   first waveform shaping means for shaping the converted object-modified wave signal from said transducer to produce a digital pulse signal;
   selection means for selecting only specified pulses in said digital pulse signal produced by said first waveform shaping means;
   second waveform shaping means for shaping said specified pulses selected by said selection means to produce a pulse signal having a predetermined pulse width shorter than the period of said clock pulse; and
   coincidence detecting means for detecting a coincidence in time between the pulse duration time of said pulse signal produced by said second waveform shaping means and a predetermined level-changing time of said clock pulse signal to generate a coincidence signal.

6. A digital type ultrasonic holography apparatus according to claim 5, wherein said selection means includes a circuit for selecting the digital pulses produced from said first waveform shaping means within a predetermined time portion of the repetition interval of said trigger pulses.

7. A digital type ultrasonic holography apparatus according to claim 6, wherein said selection means further includes a counter for selecting a specified one among said selected digital pulses.

* * * * *